United States Patent [19]

Chand

[11] 4,152,233
[45] May 1, 1979

[54] APPARATUS FOR ELECTROCHEMICAL GAS DETECTION AND MEASUREMENT

[75] Inventor: Ramesh Chand, Chatsworth, Calif.

[73] Assignee: Ambac Industries, Inc., New York, N.Y.

[21] Appl. No.: 797,350

[22] Filed: May 16, 1977

Related U.S. Application Data

[63] Continuation of Ser. No. 611,360, Sep. 8, 1977, abandoned.

[51] Int. Cl.² ............................................. G01N 27/46
[52] U.S. Cl. ................................. 204/195 P; 204/1 T
[58] Field of Search ................. 204/195 R, 195 P, 1 P

[56] References Cited

U.S. PATENT DOCUMENTS

| | | | |
|---|---|---|---|
| 2,651,612 | 9/1953 | Haller | 204/195 R |
| 2,913,386 | 11/1959 | Clark | 204/195 P |
| 3,247,452 | 4/1966 | Kordesch | 204/1 Y |
| 3,328,277 | 6/1967 | Solomons et al. | 204/195 P |
| 3,455,807 | 7/1969 | Jacobson et al. | 204/195 R |
| 3,503,861 | 3/1970 | Volpe | 204/195 P |
| 3,510,420 | 5/1970 | Mills | 204/195 P |
| 3,526,577 | 9/1970 | Molloy | 204/195 P |
| 3,629,089 | 12/1971 | Luck | 204/195 R |
| 3,696,019 | 10/1972 | Arrington et al. | 204/195 R |
| 3,707,455 | 12/1972 | Derr et al. | 204/195 P |
| 3,763,025 | 10/1973 | Chand | 204/195 P |
| 3,776,832 | 12/1973 | Oswin et al. | 204/195 R |
| 3,855,096 | 12/1974 | Bergman | 204/195 P |
| 3,894,917 | 7/1975 | Riseman et al. | 204/195 R |

*Primary Examiner*—T. Tung
*Attorney, Agent, or Firm*—Fulwider, Patton, Rieber, Lee & Utecht

[57] ABSTRACT

Method for the electrochemical detection of a gas and apparatus including a gas-contacting electrode, biased to a predetermined potential, a counter electrode and electrolyte between the electrodes. The electrochemical reaction between the sensed gas and the sensing electrode produces an electric current in a sensing circuit between the sensing electrode and the counter electrode. The sensitivity and stability of the device are maintained by including a conductive member in spaced relationship to the sensing electrode. In accordance with the method, the conductive member is biased to the same potential as the sensing electrode and is selected to have the same response to factors affecting the zero current as the sensing electrode. The conductive member is electrically connected to the sensing electrode so that their zero current outputs are continuously balanced.

9 Claims, 4 Drawing Figures

APPARATUS FOR ELECTROCHEMICAL GAS DETECTION AND MEASUREMENT

This is a contnuation, of application Ser. No. 611,360, filed Sept. 8, 1975, now abandoned.

BACKGROUND OF THE INVENTION

This invention relates generally to gas sensors and more particularly to apparatus for the electrochemical detection and measurement of gas.

The prior art includes a number of gas sensing devices for detecting certain gases and their concentrations by measuring the current generated by the electrochemical reaction of a negligible quantity of the gas. Generally, these devices include a sensing electrode maintained at a predetermined potential, non-polarizable or counter electrode, suitable circuitry and an electrolyte in contact with the electrodes. In addition, a third electrode or reference electrode may be included for stabilizing and controlling the potential of the sensing electrode.

Contact between the gas being detected and the sensing electrode results in the oxidation or reduction of the gas, depending on the potential of the sensing electrode, which generates an ionic flow between the sensing electrode and the counter electrode. The ionic flow produces a detectable current which is directly related to the concentration of the gas.

Typically, there is a flow of current between the sensing and counter electrodes even in the absence of a gas to be detected. This current flow, referred to herein as the "zero" current, is affected by changes of the potential of the sensing electrode, temperature changes within the device and by the aging of the sensing electrode over a period of time. These changes require frequent recalibration of the device and, unless compensated for, may be of sufficient magnitude to reduce the sensitivity and accuracy of the device.

In many cases, however, for example, because of limited manpower or because of the location of the device, frequent recalibration is impracticable or inconvenient. Accordingly, there is a need for a device in which zero current drift is automatically compensated for and the frequency of recalibration substantially reduced.

SUMMARY OF THE INVENTION

The present invention relates to an electrochemical gas sensing device designed to minimize zero current drift, particularly zero current drift caused by temperature changes and electrode aging. The frequency of recalibration to compensate for changes in zero current is substantially reduced and the device maintains its stability and sensitivity over a period of time and is relatively temperature insensitive.

More particularly, zero drift compensating means is provided for continuously balancing the zero current of the sensing electrode so that the output current to a meter or other recording device is essentially only that current generated by the oxidation or reduction of a gas being detected. The compensating means includes a conductive member, which is located adjacent but spaced from the gas sensing electrode and circuitry for balancing the zero current output of the sensing electrode and the conductive member.

The conductive member is selected to provide substantially the identical zero current response to temperature and time as the sensing electrode when both are set at the same potential. The conductive member is in spaced relationship with the sensing electrode so that only the sensing electrode is contacted by the gas being detected but so that the conductive member is exposed to substantially the same environmental conditions as the sensing electrode.

The conductive member is maintained at the same potential as the sensing electrode during operation of the device and the current flowing therethrough is equal to the sensing electrode zero current.

In a preferred embodiment, the conductive member is constructed of the same material as the sensing electrode so that its electrical response to changes in temperature, aging, or the like is substantially identical to the electrical response of the sensing electrode to the same factors. The sensing electrode and conductive member are connected by a differential amplification circuit which continuously balances the current output of the conductive member and the zero current of the sensing element. The present invention is adapted for use with various combinations of sensor materials, electrolytes and potentials for directing a variety of specific gases such as $O_2$, $CO$, $SO_2$, $NO$, $NO_2$, $CHO$ and alcohols.

DETAILED DESCRIPTION OF THE INVENTION

Figure 1:
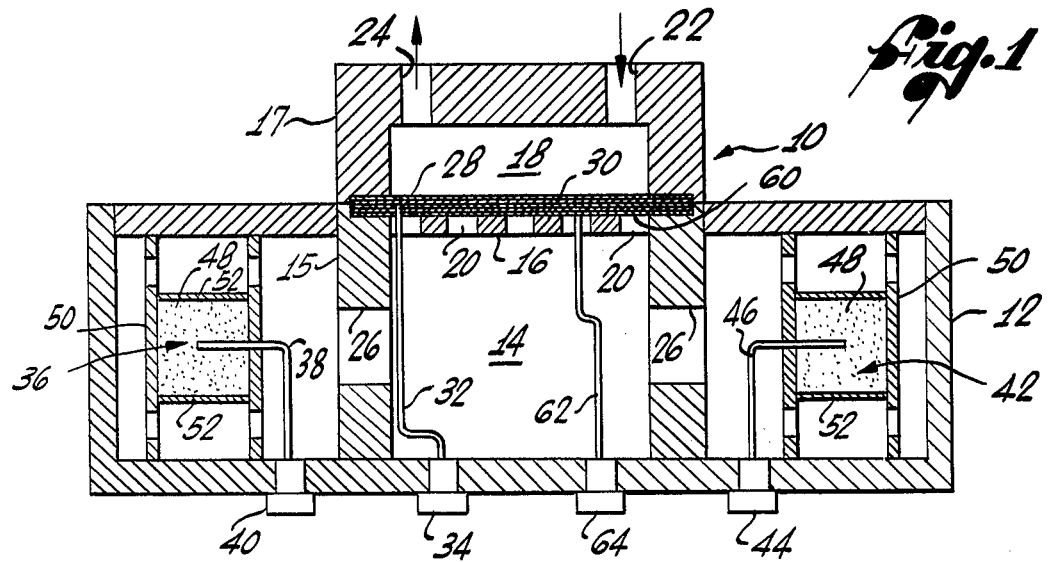
FIG. 1 is a cross-sectional view of a gas sensor constructed in accordance with the present invention.

As shown in FIG. 1, the invention is embodied in a gas sensing device, indicated generally as 10 including a hollow body 12, defining a chamber 14 for containing an electrolyte. A cylinder 15, having a closed upper end and a supporting plate 16 located adjacent the closed end, is mounted in the body 12 with its upper end portion 17 extending through the body upper wall. A sample chamber 18 is defined within the extending end portion 17 and openings 20 in the plate 16 provide communication with the chamber 14. Passages 22 and 24 are provided in the upper end portion 17 for ingress and egress respectively of a gas into the sample chamber 18 and openings 26 in the side wall located in the chamber 14 provide communication through the chamber.

The openings 20 are closed by a gas permeable, fluid tight membrane 28 under which is disposed a sensing electrode 30 which is connected by a lead wire 32 to a terminal 34. The sensing electrode 30 is preferably a porous layer of metallic particles which are bonded to the membrane to form a composite member. The composition, construction and function of such composite membrane-sensing electrode members is known in the art, for example in U.S. Pat. No. 3,510,420, and further description is deemed unnecessary.

A non-polarizable counter-electrode 36 is connected by a lead wire 38 to a terminal 40 and similarly a reference electrode 42 is connected to a terminal 44 by lead wire 46. The electrodes 36 and 42 are typically composed of a compacted powdered compound 48, for example a lead-lead sulfate mixture disposed within a vertically oriented tube 50 and secured by porous caps 52. However, in many cases a single wire electrode is used with good results. The counter electrode 36 and the reference electrode 42 may be combined as a single unit although this is not preferred since any change in the electrode would directly affect the sensing element 30 and could result in loss of stability.

Suitable circuitry is provided at the terminals 34, 40 and 44 for biasing the sensing electrode 30 to a preselected potential and for measuring current flow between the sensing electrode and the counter electrode 36. Gases entering the sample chamber 18 permeate the membrane 28 to contact the sensing electrode 30. Depending on the potential of the sensing electrode 30 and other factors well understood in the art, a particular gas will be electrochemically oxidized or reduced. This will produce a detectable current flow between the counter electrode 36 and the sensing electrode 30 which is directly related to the concentration of the reacting gas. Suitable current measuring instruments are provided for reading and recording the current flow.

When biased to a preselected potential as described, a current flow occurs between the sensing electrode 30 and the counter electrode 36 even in the absence of the reacting gas. This current flow, which is referred to as the zero current, or base current, is calibrated out of the measuring instrument so that only additions to the zero current occurring as a result of electrochemical reactions at the sensing element 30 are measured. However, zero current is subject to change or drift for a variety of reasons including the effects of aging of the sensing electrode 30 and the counter electrode 36 or changes in the internal temperature of the sensing device 10.

It has been found, for example, that the zero current may increase 10% to 15% for each centigrade degree rise in temperature and that unless the sensing device 10 is frequently recalibrated to increased zero current, the sensitivity and accuracy of the device is substantially reduced. Similar reductions in sensitivity and accuracy may occur as a result of lowering of the temperature.

In accordance with the present invention means are provided for compensating for zero current drift, or what is the same, base current drift, such as may be caused by long term changes in the electrical characteristics of the sensing electrode or by increases or decreases in the internal temperature of the device. The sensitivity and stability of electrochemical gas sensors are thereby maintained over a longer period of time and through a range of temperatures without frequent recalibration.

Figure 2:
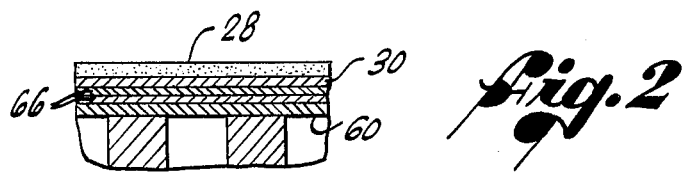
FIG. 2 is an enlarged fragmentary sectional view of the sensing electrode and conductive member of the device shown in FIG. 1 illustrating the spaced relationship therebetween.

As is shown in FIG. 1 and more particularly in FIG. 2, a conductive member 60 is located adjacent the sensing electrode 30 and spaced apart therefrom. A lead wire 62 connects the conductive member to a terminal 64. The conductive member 60 has the same electrical characteristics as the sensing electrode 30 and during operation is biased to the same potential so that its current output is related to the zero current of the sensing electrode. It is important that the conductive member 60 respond to factors affecting its current output to the same extent that the sensing electrode 30 does so that the relationship between its current output and zero current remains substantially constant for balancing purposes.

In the preferred embodiment the conductive member 60 and the sensing electrode 30 are constructed of the same materials and have substantially identical physical dimensions and the current outputs in the absence of detectable gas are substantially equal. Thus, for example, the conductive member 60 can be a porous layer of the same metal particles utilized in forming the sensing electrode 30.

The conductive member 60 is disposed adjacent the sensing electrode 30 so that it is not in contact with the gas being electrochemically reacted. This is accomplished by interposing one or more spacing layers 66 between the sensing electrode 30 and the conductive member 60. The spacing layers 66 are liquid permeable to permit the electrolyte to reach the sensing electrode 30.

The amount of spacing between the sensing electrode 30 and the conductive member 60 is not critical although there should be no physical contact therebetween. On the other hand, the conductive member 60 should not be too remote from the sensing electrode 30, in order to reduce as much as possible the period of time during which the sensing electrode 30 and the conductive member 60 are subjected to different conditions and are thus not in balance. This is particularly important where zero drift is due to changes in temperature within the device.

In the embodiment illustrated good results are achieved when the spacing is maintained between about 10 mils and about 125 mils.

As was described above, the conductive member 60 is biased to the same potential as the sensing electrode 30 so that both will generate the same or substantially the same zero current. Circuitry is provided for balancing the zero currents so that the stability and sensitivity of the device 10 is maintained despite changes in zero current.

Figure 3:
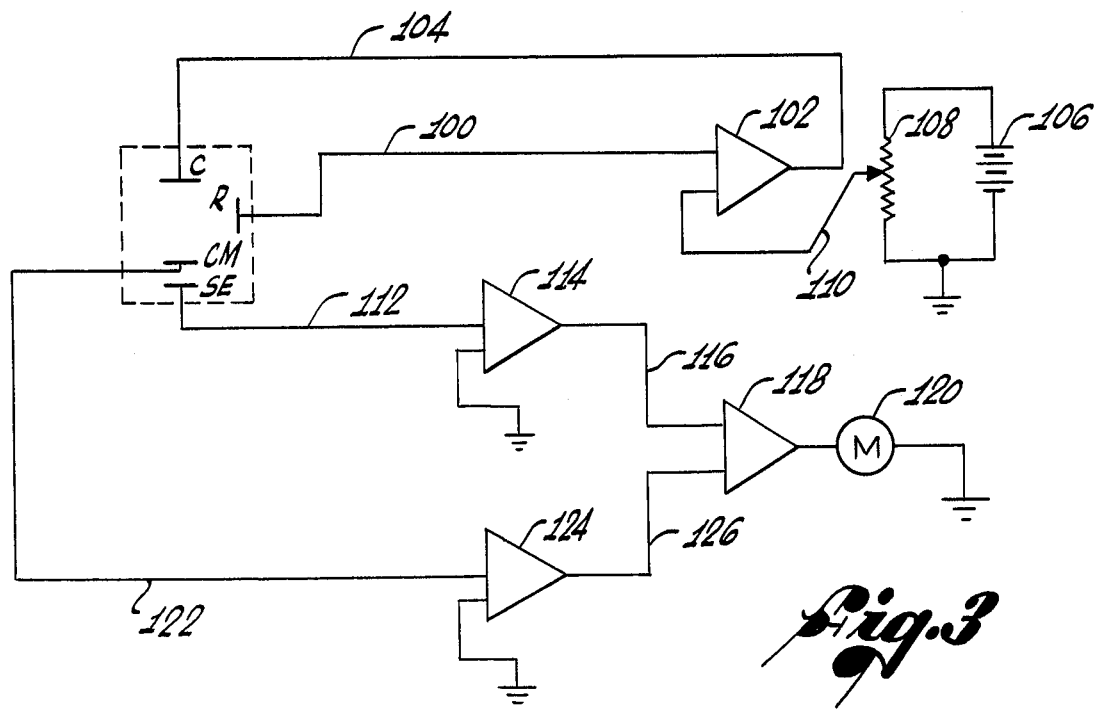
FIG. 3 is an electrical schematic diagram of circuitry for imposing a potential on the sensing electrode and the conductive member and for balancing the sensing electrode zero current and the current of the conductive member.

As shown in FIG. 3 the counter electrode (C), the reference electrode (R), the sensing electrode (SE) and the conductive member (CM) are diagrammatically represented with simplified electrical interconnections represented schematically. The reference electrode is connected by a line 100 to one input of a conventional high gain amplifier 102 and the counter electrode is connected to the output of the amplifier 102 by line 104. The counter electrode, through the electrolyte, imposes a potential on the sensing element and conductive member. The imposed potential is varied by an adjustable voltage source including a battery 106 connected across a potentiometer 108 connected to the remaining input of the amplifier 102 by a wiper arm 110. In this manner the reference electrode acts to stabilize the potential on the sensing element and conductive member but current flow therebetween is prevented by a high gain amplifier 102.

The sensing element is connected by a line 112, an amplifier 114, a line 116 to an input of a differential amplifier 118. A meter 120 is connected to the output of the differential amplifier 118 for measuring current flow between the counter electrode and the sensing element. The conductive member is similarly connected to an input of the differential amplifier 118 by a line 122, an amplifier 124 and a line 126.

When activated, and in the absence of a detectable gas, current flow to the differential amplifier 118 is substantially equal and the differential amplifier acts to balance the current flow so that no current flows to the meter 20. When in contact with a detectable gas, additional current is generated at the sensing element by the electrochemical reaction and the additional current in excess of the zero current passes through the differential amplifier 118 to the meter 120. As described, changes in the zero current of the sensing element are similarly reflected in the current output of the conductive member and the currents continue to be balanced at the differential amplifier 118. It should be clear that depending on the nature and degree of the factor causing the change in zero current and the spacing between the sensing element and the conductive member, there may be a short period during which the zero currents are not balanced. However, once the conductive member has adjusted to the changed conditions, its electrical characteristics will again approach those of the sensing element and the zero currents will be rebalanced.

While the invention has been discussed in connection with balancing equal current output from the sensing electrode and the conductive member it should be understood that the invention is applicable to those situations where the maintenance of a relationship between the current outputs is utilized for balancing purposes. Thus, for example, the invention is applicable where zero current output is twice the current output of the conductive member. It is essential, however, that the electrical characteristics of the conductive member change in the same manner as that of the sensing electrode in order to maintain the same relationship between the current outputs.

The following example demonstrates the temperature stability of an electrochemical gas sensor constructed in accordance with the invention.

EXAMPLE I

An electrochemical gas sensor was constructed in accordance with the device shown in FIG. 1 and described above. The sensing electrode was a porous layer of gold particles formed by heating a filter paper impregnated with gold chloride. A "Teflon" membrane was formed over one surface of the filter paper. The conductive member was similarly a porous layer of gold particles formed in the same manner as the sensing electrode but without the "Teflon" membrane. The spacing between the sensing electrode and the conductive member was 20 mils and was achieved by inserting two layers of filter paper between the conductive member and the sensing electrode.

The counter electrode and the reference electrode were both constructed of compacted mixture of equal parts lead-lead dioxide powder. The electrolyte was dilute (approximately 1N) sulfuric acid and the potential imposed on the sensing element and conductive member was approximately 1.3 V relative to normal hydrogen electrode.

The gas sensor was placed in an oven and heated in 10° increments to temperatures ranging between 10° C. to 40° C. Sufficient time was allowed at each incremental heating step to permit the internal temperature to come to equilibrium. Nitrogen gas was circulated through the sample chamber so that only zero current would be read at the meter. Zero current output was recorded at each heating increment.

After the foregoing test was completed, the conductive member was disconnected from the circuit and the test repeated. In this mode, the device operated as a conventional three electrode gas sensor.

Figure 4:
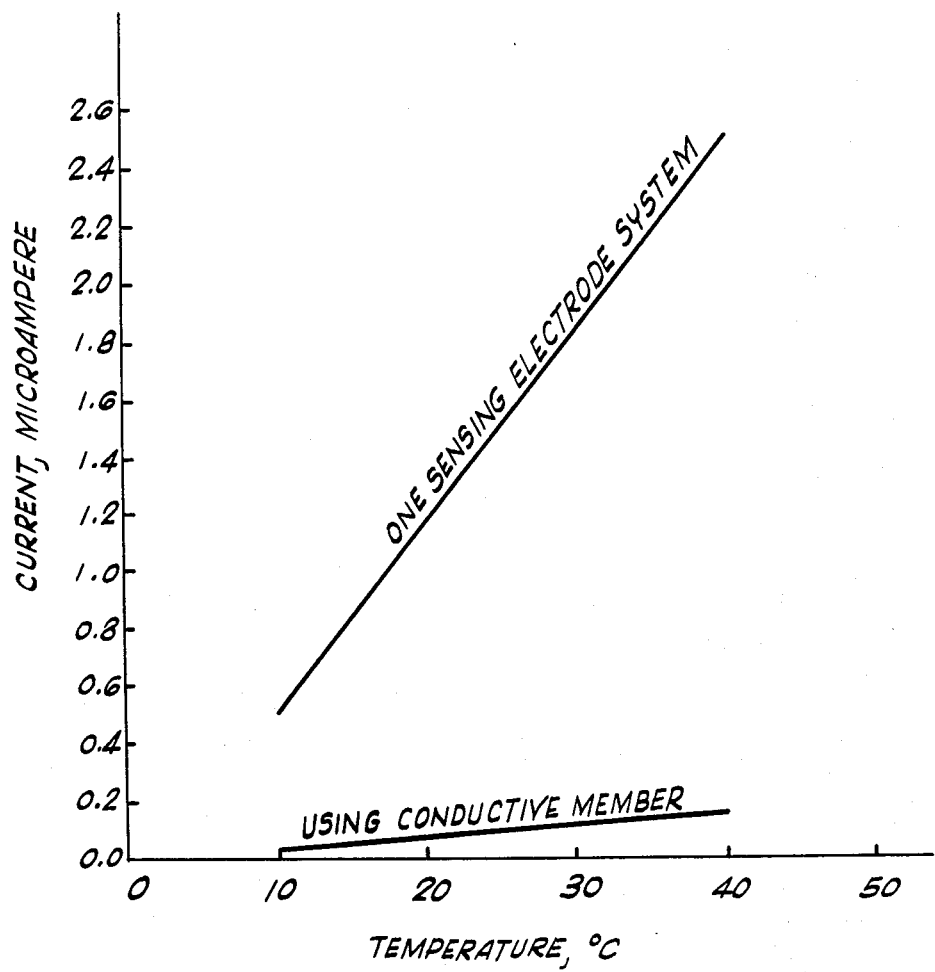
FIG. 4 is a plot of current in microamperes versus temperature illustrating the stability of a device of the present invention over a range of temperatures.

The results of the tests are illustrated in FIG. 4 which is a plot of current in microampere versus temperature °C. The line identified as ONE SENSING ELECTRODE SYSTEM represents the zero current drift without the conductive member. The line identified as WITH CONDUCTIVE MEMBER is the zero current drift of the device operating with the conductive member in the circuitry in accordance with the invention.

As shown, the device constructed in accordance with the invention exhibited a high degree of temperature stability with a total drift in zero current of about 0.10 microampere. When operated as a conventional gas sensor, zero drift over the tested temperature range was about 2.0 microampere.

The following examples illustrate various combinations of materials and different potential which may be combined in gas sensing devices in accordance with the invention for the detection of specific gases. Operation of the devices of following examples is as already described above.

TABLE A

| Example | Detected Gas | Membrane | Sensing Electrode | Conductive Member | Reference Electrode | Counter Electrode | Electrolyte | Potential in Volts with Respect to Standard Hydrogen |
|---|---|---|---|---|---|---|---|---|
| 2 | Oxides of Nitrogen | Silicone or "Teflon" | Gold | Gold | Lead wire or Lead-lead dioxide or lead sulfate | Lead sulfate- Lead Dioxide or Lead-lead dioxide | 1N $H_2SO_4$ or 1N $H_2PO_3$ or 1N acetic acid | 1.1 – 1.6 |
| 3 | $SO_2$ | Silicone or "Teflon" | Gold | Gold | lead wire or lead-lead dioxide-lead sulfate | lead sulfate- lead dioxide | 1N $H_2SO_4$ $H_2PO_3$ or acetic acid | 0.9 – 1.1 |
| 4 | $NO_2$ | Silicone or "Teflon" | Silver or gold | Silver or gold | lead wire or silver wire or mercury-mercury chloride lead-lead sulfate | mercury-mercury chloride or lead-lead sulfate | 1N KCl or $K_2SO_4$ | 0.5 – 0.9 |
| 5 | $O_2$ | Silicone or "Teflon" | Silver or gold | Silver or | Lead wire | Lead or Lead- | 1N NaOH, KOH or | between −0.3 and −0.6 |

TABLE A-continued

| Example | Detected Gas | Membrane | Sensing Electrode | Conductive Member | Reference Electrode | Counter Electrode | Electrolyte | Potential in Volts with Respect to Standard Hydrogen |
|---|---|---|---|---|---|---|---|---|
| 6 | CO | Silicone or "Teflon" | Platinum | gold Platinum | oxide lead wire or lead dioxide-lead sulfate or lead-lead sulfate | lead lead-lead sulfate or lead dioxide-lead sulfate | $K_2Co_3$ $1N\ H_2So_4$ or $H_2Po_3$ or acetic acid | 1.1 – 1.4 |
| 7 | formaldehyde | Silicone or "Teflon" | gold or silver | gold or silver | lead or silver wire or mercury-mercury oxide | lead-lead oxide or or silver-silver oxide or mercury-mercury oxide | 5%–30% aqueous solution KOH or NaOH | between —0.3 and +0.2 |
| 8 | Ethyl alcohol | silicone or "Teflon" | gold or silver | gold or silver | lead or silver wire or mercury-mercury oxide | lead-lead oxide or silver-silver oxide or mercury-mercury oxide | 5%–30% aqueous solution of KOH or NaOH | 0.2 – 0.5 |

From the foregoing it can be seen that in accordance with the present invention a method and apparatus are provided for the electrochemical detection of specific gases in which zero current drift is balanced. Accordingly, the sensitivity and stability is maintained without the necessity of frequent recalibration and the method and apparatus are substantially independent of the effects of time and temperature on zero current drift.

While the invention has been described in connection with certain preferred embodiments thereof, it should be appreciated that various modifications may be made without departing from the spirit and scope of the invention described above and defined in the appended claims.

I claim:

1. Apparatus for electrochemically detecting a particular gas in a gas sample, said apparatus comprising:

a closed container including an electrolyte and having a wall portion thereof adapted for permeation of a gas sample therethrough;

an electrically conductive gas sensing electrode within said closed container and secured adjacent said wall portion for contacting a gas sample permeating through said wall portion;

a counter electrode located in said container and spaced apart from said sensing electrode;

a reference electrode located in said container and spaced apart from said sensing electrode;

first electrical circuit means connected to said counter electrode and to said reference electrode and adapted to impose on said gas sensing electrode a selected reference potential, said reference potential producing, in the absence of a gas to be detected, a base current flow between said gas sensing electrode and said counter electrode, while producing substantially no current flow between said gas sensing electrode and said reference electrode;

compensating means for correcting for base current drift in said apparatus, said compensating means including a conductive member interposed between said gas sensing electrode and said counter electrode, and located within said container closely adjacent said gas sensing electrode and in contact with said electrolyte, said conductive member having substantially the same electrical characteristics and physical dimensions as said gas sensing electrode and being subject to the reference potential imposed on said gas sensing electrode to produce a compensating current flow between said gas sensing electrode and said conductive member which has a substantially constant relationship to said base current;

spacer means interposed between said gas sensing electrode and said conductive member, said spacer means being permeable to said electrolyte to permit said electrolyte to reach said sensing electrode, and being impermeable to gas to be detected to prevent such gas from reaching said conductive member;

and second electrical circuit means including a differential amplifier connected to said gas sensing electrode and to said conductive member for subtracting the current flow between said gas sensing and counter electrodes from the current flow between said conductive member and said counter electrode, whereby the presence of said base current is balanced by said compensating current and any base current drift is automatically balanced by a corresponding drift in said compensating current, to maintain the sensitivity and stability of said apparatus over a relatively long period of time and a relatively wide range of temperatures, the resultant current from said differential amplifier being a current produced by said gas sensing electrode in response to gas samples containing the gas to be detected, the magnitude of the resultant current being related to the concentration of the gas to be detected.

2. Apparatus as set forth in claim 1, wherein said sensing electrode and said conductive member are each comprised of a porous, electrically conductive metallic layer.

3. Apparatus as set forth in claim 2, wherein said sensing electrode further includes a gas-permeable liquid-impermeable membrane disposed on a surface thereof, said membrane defining said gas permeable portion of the wall of said container.

4. Apparatus as set forth in claim 1, wherein said sensing electrode and said conductive member are spaced apart between about 10 mils and about 125 mils.

5. Apparatus as set forth in claim 1, wherein said sensing electrode and said conductive member are spaced apart about 20 mils.

6. Apparatus as set forth in claim 1, wherein said sensing electrode and said conductive member are polarizable and said counter electrode is non-polarizable.

7. Apparatus as set forth in claim 1, wherein said conductive member has sufficiently similar physical characteristics and is located sufficiently close to said gas sensing electrode to respond to factors affecting its current output to the same extent that said gas sensing electrode responds.

8. The apparatus of claim 1, wherein said gas sensing electrode and said conductive member are constructed of the same materials and have substantially identical physical dimensions.

9. The apparatus of claim 1, wherein said first electrical circuit means includes a high gain amplifier having a first input connected to said reference electrode, a second input connected to an adjustable voltage source, and an output connected to said counter electrode, said high gain amplifier supplying a selectable potential to said counter electrode, and said reference electrode stabilizing the potential imposed by said counter electrode on said gas sensing electrode.

* * * * *